United States Patent
Chen et al.

(10) Patent No.: US 11,306,313 B2
(45) Date of Patent: ＊Apr. 19, 2022

(54) PEPTIDE, COMPLEX OF PEPTIDE AND SIRNA, AND METHODS OF USE THEREOF

(71) Applicants: Positec Power Tools (Suzhou) Co., Ltd, Jiangsu Province (CN); Pu Chen, Waterloo (CA)

(72) Inventors: Pu Chen, Waterloo (CA); Dafeng Chu, Waterloo (CA); Baoling Chen, Waterloo (CA); Wen Xu, Kitchener (CA); Ran Pan, Waterloo (CA)

(73) Assignees: Positec Power Tools (Suzhou) Co LTD, Jiangsu Province (CN); Pu Chen, Waterloo (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/751,783

(22) Filed: Jan. 24, 2020

(65) Prior Publication Data

US 2020/0190518 A1    Jun. 18, 2020

Related U.S. Application Data

(63) Continuation of application No. 16/110,713, filed on Aug. 23, 2018, now abandoned, which is a continuation of application No. 15/106,108, filed as application No. PCT/CN2014/094198 on Dec. 18, 2014, now Pat. No. 10,076,575.

(30) Foreign Application Priority Data

Dec. 18, 2013 (CN) .................. 201310698871.0

(51) Int. Cl.
| | | |
|---|---|---|
| C12N 15/113 | (2010.01) | |
| A61K 47/42 | (2017.01) | |
| C07K 14/47 | (2006.01) | |
| A61K 9/51 | (2006.01) | |
| C12N 15/11 | (2006.01) | |
| C12N 15/87 | (2006.01) | |
| A61K 31/713 | (2006.01) | |
| A61K 47/64 | (2017.01) | |

(52) U.S. Cl.
CPC .......... *C12N 15/113* (2013.01); *A61K 9/5169* (2013.01); *A61K 31/713* (2013.01); *A61K 47/42* (2013.01); *A61K 47/64* (2017.08); *C07K 14/47* (2013.01); *C12N 15/111* (2013.01); *C12N 15/87* (2013.01); *C12N 2310/14* (2013.01); *C12N 2310/3513* (2013.01); *C12N 2320/32* (2013.01)

(58) Field of Classification Search
CPC ...... G01N 1/30; G01N 1/36; G01N 2001/302; G01N 2001/307; G01N 2333/95; G01N 33/582; G01N 33/6803; A61K 31/713; A61K 47/42; A61K 47/64; A61K 9/5169; A61P 35/00; C07K 14/47; C12N 15/111; C12N 15/113; C12N 15/87; C12N 2310/14; C12N 2310/3513; C12N 2320/32

See application file for complete search history.

(56) References Cited

U.S. PATENT DOCUMENTS

| | | | |
|---|---|---|---|
| 9,259,483 | B2 | 2/2016 | Chen et al. |
| 9,603,946 | B2 | 3/2017 | Chen et al. |
| 9,608,946 | B2 | 3/2017 | MacDonald |
| 9,950,073 | B2 | 4/2018 | Chen et al. |
| 10,076,575 | B2 | 9/2018 | Chen et al. |
| 2016/0271258 | A1 | 9/2016 | Jakymiw et al. |
| 2017/0128582 | A1 | 5/2017 | Chen et al. |

FOREIGN PATENT DOCUMENTS

| | | |
|---|---|---|
| CN | 103272242 A | 9/2013 |
| WO | 2009002274 A1 | 12/2008 |
| WO | 2009026729 A1 | 3/2009 |
| WO | 2009046220 A2 | 4/2009 |
| WO | 2011020188 A1 | 2/2011 |
| WO | 2012137036 A1 | 10/2012 |
| WO | 2013075244 A1 | 5/2013 |

OTHER PUBLICATIONS

Balazs, et al.; "Liposomes for Use in Gene Delivery," Journal of Drug Delivery; vol. 2011, Article ID 326497, 12 pages.
Vonarbourg, et al.; "Parameters influencing the stealthiness of colloidal drug delivery systems," Biomaterials (2006), vol. 27, pp. 4356-4373.
Cartier, et al.; "Utilization of synthetic peptides containing nuclear localization signals for nonviral gene transfer systems," Gene Therapy (2002), vol. 9, pp. 157-167.
Chou, et al.; "Structural and Functional Role of Leucine Residues in Proteins," Journal of Molecular Biology (1973), vol. 74, pp. 263-281.
Damen, et al.; "Delivery of DNA and siRNA by novel gemini-like amphiphilic peptides,"; Journal of Controlled Release (2010), vol. 145, pp. 33-39.
Engelke, et al.; "RNA interference; Methods in enzymology."; Elsevier Academic Press: San Diego; (2005), vol. 392, pp. 1-453.
Fire, et al.; "Potent and specific genetic interference by double-stranded RNA in Caenorhabditis elegans,"; Nature (1998); vol. 391, pp. 806-811.
Futaki, et al.; "Arginine-rich Peptides. An Abundant Source of Membrane-Permeable Peptides Having Potential as Carriers for Intracellular Protein Delivery,"; The Journal of Biological Chemistry (2001); vol. 276, No. 8, pp. 5836-5840.

(Continued)

*Primary Examiner* — Marcela M Cordero Garcia
(74) *Attorney, Agent, or Firm* — Dunlap Codding, P.C.

(57) ABSTRACT

A series of peptides and a peptide-siRNA complex are disclosed, wherein the peptide based complex effectively enhances delivery of siRNA molecules into the cells and release of siRNA in the cell, and improves siRNA mediated gene silencing efficiency of cellular targets. Pharmaceutical compositions that include the complex, as well as a use of the complex in the gene therapy field, are also disclosed.

20 Claims, 4 Drawing Sheets

Specification includes a Sequence Listing.

(56) References Cited

OTHER PUBLICATIONS

Järver, et al.; "Applications of cell-penetrating peptides in regulation of gene expression," Biochemical Society Transactions, (2007), vol. 35, Part 4, pp. 770-774.
Khalil, et al.; "Mechanism of improved gene transfer by the N-terminal stearylation of octaarginine; enhanced cellular association by hydrophobic core formation," Gene Therapy (2004), vol. 11, pp. 636-644.
Langel, Ü.; "Handbook cell-pentrating peptides," 2nd Edition; CRC Press Taylor & Francis Group; Boca Raton, FL (2007), pp. 1-600.
Lehto, et al.; "Delivery of nucleic acids with a stearylated (RxR)4 peptide using a non-covalent co-incubation strategy,"; Journal of Controlled Release, (2010), vol. 141, pp. 42-51.
Lo, et al.; "An endosomolytic Tat peptide produced by incorporation of histidine and cysteine residues as a nonviral vector for DNA transfection,"; Biomaterials (2008), vol. 29, pp. 2408-2414.
Lundberg, et al.; "Delivery of short interfering RNA using endosomolytic cell-penetrating peptides,"; The Journal of the Federation of American Societies for Experimental Biology; (2007), vol. 21, No. 11, pp. 2664-2671.
Mahato, Ram I.; "Biomaterials for delivery and targeting of proteins and nucleic acids,"; CRC Press: Boca Raton (2005), pp. 1-681.
Manoharan, M.; "RNA interference and chemically modified small interfering RNAs," Current Opinion Chemical Biology; (2004); vol. 8, pp. 570-579.
Moghimi, et al.; "Subcutaneous and intravenous delivery of diagnostic agents to the lymphatic system: applications in lymphoscintigraphy and indirect lymphography,"; Advanced Drug Delivery Reviews (1999), vol. 37, pp. 295-312.
Mok, et al.; "Self-Crosslinked and Reducible Fusogenic Peptides for Intracellular Delivery of siRNA," Biopolymers (2008), vol. 89, No. 10, pp. 881-888.
Novina, et al.; "The RNAi revolution," Nature (2004), vol. 430, pp. 161-164.
Oehlke, et al.; "Cellular uptake of an α-helical amphipathic model peptide with the potential to deliver polar compounds into the cell interior non-endocytically", Biochimica et Biophysica Acta (1998), vol. 1414, pp. 127-139.
Oliveira, et al.; "Targeted delivery of siRNA,"; Journal of Biomedicine and Biotechnology (2006), Article ID 63675, pp. 1-9.
Orlacchio, et al.; "RNA interference as a Tool for Alzheimer's Disease Therapy," Mini Reviews in Medicinal Chemistry (2007), vol. 7, pp. 1166-1176.
Paddison, et al.; "RNA interference: Current topics in microbiology and immunology," Springer: Berlin (2008), vol. 320, pp. 1-273.
Tanaka, et al.; "Disulfide crosslinked stearoyl carrier peptides containing arginine and histidine enhance siRNA uptake and gene silencing,"; International Journal of Pharmaceutics (2010), No. 398, pp. 219-224.
Verma, et al.; "Functional tuning of nucleic acids by chemical modificaitons: Tailored oligonucleotides as drugs, devices and diagnostics,"; The Chemical Record (2003), vol. 3, No. 1, pp. 51-60.
Vives, E.; "Present and future of cell-penetrating peptide mediated delivery systems: is the Trojan horse too wild to go only to Troy?,"; Journal of Controlled Release, (2005), vol. 109, Nos. 1-3, pp. 77-85.
Wang, et al.; "Arginine-rich intracellular delivery peptides noncovalently transport protein into living cells," Biochemical and Biophysical Research Communications, (2006), vol. 346, pp. 758-767.
Zhang, et al.; "RNA interference with chemically modified siRNA," Current Topics Medicinal Chemistry, (2006), vol. 6, pp. 893-900.
International Search Report, dated Mar. 13, 2015, in PCT/CN2014/94198, filed Dec. 18, 2014.
Written Opinion of the International Searching Authority, dated Mar. 13, 2015, in PCT/CN2014/94198, filed Dec. 18, 2014.
EP14872058; Chen, et al.; Supplementary European Search Report dated Jul. 5, 2017, filed Dec. 18, 2014; 19 pages.
Chu, et al.; "Rational Modification of Oligoarginine for Highly Efficient siRNA Delivery: Structure-Activity Relationship and Mechanism of Intracellular Trafficking of siRNA," Nanomedicine: Nanotechnology, Biology, and Medicine (2015), (published Sep. 2, 2014); vol. 11, pp. 435-446.
Langlet-Bertin, et al.; "Design and Evaluation of Histidine-Rich Amphipathic Peptides for siRNA Delivery," Pharm Res (2010), vol. 27, pp. 1426-1436.
Tanaka, et al.; "Disulfide Crosslinked Stearoyl Carrier Peptides Containing Arginine and Histidine Enhance SiRNA Uptake and Gene Silencing," International Journal of Pharmaceutics (2010), vol. 398, pp. 219-224.
Guo, et al.; "Cationic Micelles Self Assembled from Cholesterol-Conjugated Oligopeptides as an Efficient Gene Delivery Vector," Biomaterials (2008) vol. 29, pp. 4838-4846.
U.S. Appl. No. 16/110,713; Pu Chen; filed Aug. 23, 2018; Office Action dated Jul. 26, 2019.
Potter, et al.; "Transfectoin by Electroporation." Current Protoc Mol Biol (2003) Chapter: Unit 9.3, pp. 1-12.
Classic Protocol. "Transfection of mammalian cells by electroporation," Nature Methods (2006), vol. 3, No. 1, pp. 67-68.
Technical Resources. 21127—Ham's F-12K (Kalghn's). https://www.thermofisher.com/us/en/home/technical-resources/media-formulation.65.html (2019) accessed online on Jul. 22, 2019, pp. 1-3.
U.S. Appl. No. 15/106,108, Pu Chen, filed Jun. 17, 2016,;Office Action dated Jan. 11, 2018.
U.S. Appl. No. 15/106,108, Pu Chen, filed Jun. 17, 2016; Amendment and Response to Office Action filed Apr. 10, 2018.
U.S. Appl. No. 15/106,108, Pu Chen, filed Jun. 17, 2016; Notice of Allowance dated May 16, 2018.
EP14872058; Chen, et al.; European Search Report dated Jul. 5, 2017; filed Nov. 2, 2016.
EP14872058; Chen, et al.; Response to Written Opinion dated Jan. 26, 2018, filed Nov. 2, 2016.
EP14872058; Chen, et al.; Examination Report dated Apr. 11, 2018, filed Nov. 2, 2016.
EP14872058; Chen, et al.; Response to Examination Report dated Aug. 15, 2018, filed Nov. 2, 2016.
EP14872058; Chen, et al.; Decision to Grant dated Apr. 26, 2019, filed Nov. 2, 2016.

SEQUENCE LISTING

```
<160> NUMBER OF SEQ ID NOS: 15

<210> SEQ ID NO 1
<211> LENGTH: 22
<212> TYPE: PRT
<213> ORGANISM: Artificial sequence
<220> FEATURE:
<223> OTHER INFORMATION: synthetic sequence - peptide GL5

<400> SEQUENCE: 1

Gly Leu Trp His Ala Trp Leu Trp His Ala Phe Leu Ala Ser His Arg
1               5                   10                  15

Leu Leu Arg Leu Leu Arg
            20

<210> SEQ ID NO 2
<211> LENGTH: 12
<212> TYPE: PRT
<213> ORGANISM: Artificial sequence
<220> FEATURE:
<223> OTHER INFORMATION: Synthetic sequence - B of peptide STR-KV

<400> SEQUENCE: 2

His His His Lys Lys Lys Val Val Val Val Val Val
1               5                   10

<210> SEQ ID NO 3
<211> LENGTH: 24
<212> TYPE: PRT
<213> ORGANISM: Artificial sequence
<220> FEATURE:
```

-continued

<223> OTHER INFORMATION: Synthetic sequence - B of peptide STR-HR

<400> SEQUENCE: 3

His His His His His His His His His His His His
1               5                   10                  15

Arg Arg Arg Arg Arg Arg Arg Arg
            20

<210> SEQ ID NO 4
<211> LENGTH: 18
<212> TYPE: PRT
<213> ORGANISM: Artificial sequence
<220> FEATURE:
<223> OTHER INFORMATION: Synthetic sequence - B of peptide STR-C6M1

<400> SEQUENCE: 4

Arg Leu Trp Arg Leu Leu Trp Arg Leu Trp Arg Arg Leu Trp Arg Leu
1               5                   10                  15

Leu Arg

<210> SEQ ID NO 5
<211> LENGTH: 18
<212> TYPE: PRT
<213> ORGANISM: Artificial sequence
<220> FEATURE:
<223> OTHER INFORMATION: Synthetic sequence - B of peptide STR-C

<400> SEQUENCE: 5

Arg Leu Trp His Leu Leu Trp Arg Leu Trp Arg Arg Leu His Arg Leu
1               5                   10                  15

Leu Arg

<210> SEQ ID NO 6
<211> LENGTH: 21
<212> TYPE: DNA
<213> ORGANISM: Artificial sequence
<220> FEATURE:
<223> OTHER INFORMATION: Synthetic sequence - primer for mouse GADPH
      gene

<400> SEQUENCE: 6
ttgctgttga agtcgcagga g                                          21

<210> SEQ ID NO 7
<211> LENGTH: 20
<212> TYPE: DNA
<213> ORGANISM: Artificial sequence
<220> FEATURE:
<223> OTHER INFORMATION: Synthetic sequence - primer for mouse GADPH
      gene

<400> SEQUENCE: 7
tgtgtccgtc gtggatctga                                            20

<210> SEQ ID NO 8
<211> LENGTH: 24
<212> TYPE: DNA
<213> ORGANISM: Artificial sequence
<220> FEATURE:
<223> OTHER INFORMATION: Synthetic sequence - primer for mouse
      cyclophilin

<400> SEQUENCE: 8
agggtttctc cacttcgatc ttgc                                       24

```
<210> SEQ ID NO 9
<211> LENGTH: 24
<212> TYPE: DNA
<213> ORGANISM: Artificial sequence
<220> FEATURE:
<223> OTHER INFORMATION: Synthetic sequence - primer for mouse
      cyclophilin

<400> SEQUENCE: 9
agatggcaca ggaggaaaga gcat                                           24

<210> SEQ ID NO 10
<211> LENGTH: 35
<212> TYPE: PRT
<213> ORGANISM: Artificial sequence
<220> FEATURE:
<223> OTHER INFORMATION: Synthetic sequence - peptide GL5-M
<220> FEATURE:
<221> NAME/KEY: MISC_FEATURE
<222> LOCATION: (4)..(8)
<223> OTHER INFORMATION: Up to four of these Histidine residues may be
      absent
<220> FEATURE:
<221> NAME/KEY: MISC_FEATURE
<222> LOCATION: (13)..(17)
<223> OTHER INFORMATION: Up to four of these Histidine residues may be
      absent
<220> FEATURE:
<221> NAME/KEY: MISC_FEATURE
<222> LOCATION: (23)..(28)
<223> OTHER INFORMATION: Up to five of these Histidine residues may be
      absent

<400> SEQUENCE: 10

Gly Leu Trp His His His His His Ala Trp Leu Trp His His His
1               5                   10                  15

His Ala Phe Leu Ala Ser His His His His His Arg Leu Leu Arg
            20                  25                  30

Leu Leu Arg
        35

<210> SEQ ID NO 11
<211> LENGTH: 24
<212> TYPE: PRT
<213> ORGANISM: Artificial sequence
<220> FEATURE:
<223> OTHER INFORMATION: Synthetic sequence - peptide STR-KV-M
<220> FEATURE:
<221> NAME/KEY: MISC_FEATURE
<222> LOCATION: (1)..(8)
<223> OTHER INFORMATION: Up to five of these Histidine residues may be
      absent
<220> FEATURE:
<221> NAME/KEY: MISC_FEATURE
<222> LOCATION: (9)..(16)
<223> OTHER INFORMATION: Up to five of these Lysine residues may be
      absent
<220> FEATURE:
<221> NAME/KEY: MISC_FEATURE
<222> LOCATION: (17)..(24)
<223> OTHER INFORMATION: Up to two of these Valine residues may be
      absent

<400> SEQUENCE: 11

His His His His His His His His Lys Lys Lys Lys Lys Lys Lys Lys
1               5                   10                  15

Val Val Val Val Val Val Val Val
            20
```

```
<210> SEQ ID NO 12
<211> LENGTH: 50
<212> TYPE: PRT
<213> ORGANISM: Artificial sequence
<220> FEATURE:
<223> OTHER INFORMATION: Synthetic sequence - peptide STR-HR-M
<220> FEATURE:
<221> NAME/KEY: MISC_FEATURE
<222> LOCATION: (1)..(30)
<223> OTHER INFORMATION: Up to 22 of these Histidine residues may be
      absent
<220> FEATURE:
<221> NAME/KEY: MISC_FEATURE
<222> LOCATION: (31)..(50)
<223> OTHER INFORMATION: Up to 12 of these Arginine residues may be
      absent

<400> SEQUENCE: 12

His His His His His His His His His His His His His His His
1               5                   10                  15

His His His His His His His His His His His His His His Arg Arg
                20                  25                  30

Arg Arg Arg Arg Arg Arg Arg Arg Arg Arg Arg Arg Arg Arg Arg
        35                  40                  45

Arg Arg
    50

<210> SEQ ID NO 13
<211> LENGTH: 24
<212> TYPE: PRT
<213> ORGANISM: Artificial sequence
<220> FEATURE:
<223> OTHER INFORMATION: Synthetic sequence - peptide GL1

<400> SEQUENCE: 13

Gly Leu Trp Arg Ala Trp Leu Trp Lys Ala Phe Leu Ala Ser Asn Trp
1               5                   10                  15

Arg Arg Leu Leu Arg Leu Leu Arg
            20

<210> SEQ ID NO 14
<211> LENGTH: 16
<212> TYPE: PRT
<213> ORGANISM: Artificial sequence
<220> FEATURE:
<223> OTHER INFORMATION: Synthetic sequence - hydrophobic domain of
      peptide GL1

<400> SEQUENCE: 14

Gly Leu Trp Arg Ala Trp Leu Trp Lys Ala Phe Leu Ala Ser Asn Trp
1               5                   10                  15

<210> SEQ ID NO 15
<211> LENGTH: 8
<212> TYPE: PRT
<213> ORGANISM: Artificial sequence
<220> FEATURE:
<223> OTHER INFORMATION: Synthetic sequence - cationic domain of peptide
      GL1

<400> SEQUENCE: 15

Arg Arg Leu Leu Arg Leu Leu Arg
1               5
```

PEPTIDE, COMPLEX OF PEPTIDE AND SIRNA, AND METHODS OF USE THEREOF

CROSS REFERENCE TO RELATED APPLICATIONS/INCORPORATION BY REFERENCE STATEMENT

This application is a continuation of U.S. Ser. No. 16/110,713, filed Aug. 23, 2018, now abandoned; which is a continuation of U.S. Ser. No. 15/106,108, filed Jun. 17, 2016, now U.S. Pat. No. 10,076,575, issued Sep. 18, 2018; which is a US national stage application filed under 35 USC § 371 of International Application No. PCT/CN2014/094198, filed Dec. 18, 2014; which claims priority to Chinese Application No. CN 201310698871.0, filed Dec. 18, 2013. The entire contents of each of the above-referenced applications are hereby expressly incorporated herein by reference.

BACKGROUND

Over the past decade, we have witnessed tremendous progress in our understanding of the role of RNA molecules in the regulation of gene expression. The main contribution to this progress was offered by the discovery of RNA interference (RNAI). First identified in C. elegans by Fire and Mello, RNAi is an evolutionary conserved mechanism that brings about a sequence specific, post transcriptional gene silencing (PTGS) through the use of short RNAs. RNA interference (RNAi) is a short interfering RNA (siRNA) mediated gene silencing technology with specific sequence. siRNA is duplex small molecule consisting of 21-23 nucleotides. Because RNAi has efficient and specific effect on gene silencing to disease, it has been gradually developed to a new gene treatment method for inherited or acquired diseases which includes viral infections and cancer, and so on. Till now, a lot of animal treatment experiments and clinical trials have been carried out on using siRNA to treat disease.

The major limitations for the use of siRNA both in vitro and in vivo are the instability of naked siRNA in physiological conditions, rapid clearance from the bloodstream, and the inability to cross the cellular membrane to gain access to the intracellular environment. Although siRNA has shown good silencing effect on in vitro application research and the cell level, because of its large molecular weight and a large number of negative charges carried by itself, it is not able to penetrate through the cell membrane and enter into the cell, non-unique target losing effects and immune response will be initiated in the transportation. In the meanwhile, it also faces some other obstacles, such as nuclease degradation and so on, which results tremendous challenges in diseases treatment for siRNA transport system. So the transfection of siRNA has become the main bottleneck and restricted its application. How to enhance the ability of siRNA to penetrate the cell membrane and improve its stability and targeting in vivo are the urgent problems to be solved in siRNA drug carrier. So safe and effective siRNA drug carrier design and synthetise has become an important direction on siRNA drug research and development. Chemical modifications in the sugars, nucleobases, and the phosphate ester backbone of siRNA have been applied to improve its nuclease resistance without interfering with the silencing efficiency. Conjugation with hydrophobic functional groups has also enhanced the cellular uptake.

In comparison with chemical modifications of NAs, carrier-mediated strategies are emerging as a simple and fast means to formulate NA therapeutics and protect them from degradation. The carriers, including viral vectors and non-viral vectors, co-assembled or covalently conjugated with siRNA, The carriers are designed to enhance cell targeting, prolong drug circulation time, and improve membrane permeation. Because of the potential safety problems and high cost, wide range of clinical applications o viral vectors are greatly limited. Common delivery carrier of non-viral gene drug is positively charged cationic compound, it includes polycation, positively charged phospholipids, chitosan, albumin, dendritic macromolecules and peptide, etc., they compress the gene to assembled particles by the positively charged groups and the negatively charged phosphate groups on DNA/RNA, and make gene smoothly pass through all kinds of obstacles to complete the gene transfer, such as immune system escape, cell membrane penetration, endosome release, and so on. Although there are some arguments on what is a clear relationship between the construction and properties and transfection efficiency of DNA/RNA complexes there are still a lot of conditions determining the biocompatibility and the efficiency of the transfer DNA/RNA of the complexes according to experience. RNA/DNA carrier system formed by simple mixture and only electrostatic interactions is not stable, so a more stable and suitable sized carrier system is prerequisite to be designed for gene drugs to have good effect the of gene drugs.

As a kind of biological molecules, peptides have a lot of advantages to be a gene carrier that synthetic polymers does not have. Peptides have 20 kinds of amino acids that have different characteristics to form a primary sequence with tremendous properties; Beta folding, alpha helix and other secondary structure is obtainable by sequence design. Molecular with high purity, simple distribution and clear structure is obtainable by solid-phase synthesis. It is easy to be modified or connected to cellular target sequence, and enhance specificy. Peptides have been employed to deliver synthetic drugs, small molecules, bioactive peptides, therapeutic proteins, and NAs by a mechanism that has not yet been fully understood. These peptides may include protein-derived cell penetrating peptides (CPPs), cationic peptides, designed amphiphilic peptides, fusogenic peptides, cell targeting peptides (CTP) and peptides containing a nuclear localization signal. Cationic peptides rich in basic amino acids can electrostatically interact with small NAs or condense NA into small stable particles. CPPs can facilitate the translocation of the complex through the cell membrane. Histidine-rich pH-sensitive or fusogenic peptides can enhance the endosomal escape and cytoplasmic release of the gene complex. Involvement of CTPs in gene delivery systems mediates cell and/or tissue-specific targeting. Finally, attachment of a NLS peptide improves nuclear localization of the gene complex.

Although researches on siRNA drug delivery carrier has made some breakthroughs and developments, there are still some key issues need to be resolved to make siRNA drugs successfully been used in treatment of human diseases. For example, toxicity, specificity, targeting, immune stimulation, low transfection efficiency, and so on. Thus, because biodegradable and bicharacteristic peptide carrier can effectively combine and protect siRNA molecules to enhance cellular uptake of siRNA molecules, and improve its stability and targeting, and effectively release siRNA molecules, and reach the purpose of treatment, it makes such carrier has better advantage and application prospect in siRNA drug delivery.

DETAILED DESCRIPTION

Figure 1:
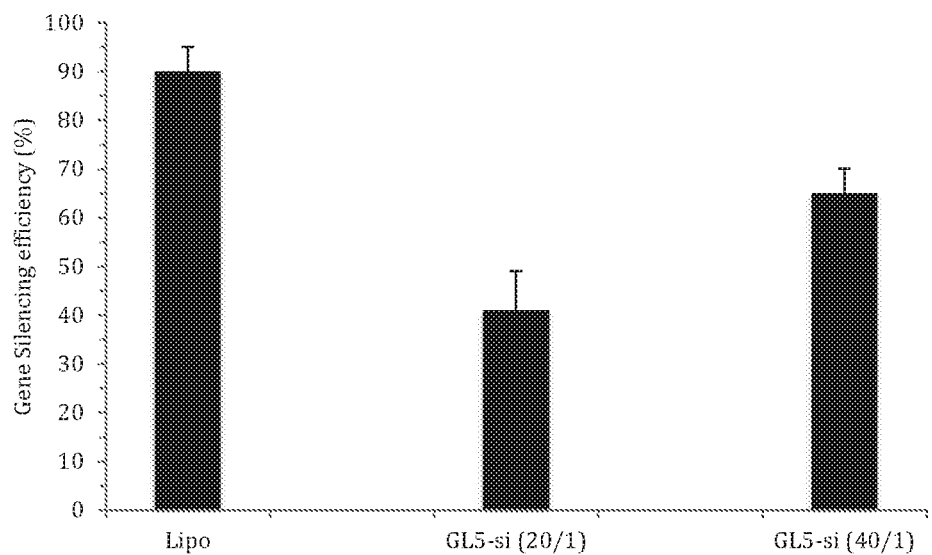
FIG. 1 illustrates the silencing efficiency of GL5/siRNA complexes with molar ratio 20/1 and 40/1 in CHO cells with siRNA concentrations of 50 nM.

The presently disclosed and/or claimed inventive concept(s) is to provide a peptide, the peptide can be used to form a complex with siRNA for gene delivery.

In order to solve the above technical problem, the presently disclosed and/or claimed inventive concept(s) provides: a peptide comprising hydrophobic part and hydrophilic part, wherein the hydrophilic part comprises a positively charged amino acid residues.

In certain non-limiting embodiments, the total number of amino acid residues contained in the peptide is 8-50.

In certain non-limiting embodiments, the peptide has the formula: GLWHxAWLWHyAFLASHzRLLRLLR; wherein $1 \leq x \leq 5$, $1 \leq y \leq 5$, $1 \leq z \leq 6$; and wherein x, y, and z are integers (SEQ ID NO:10).

In certain non-limiting embodiments, the nitrogen terminal of the peptide is acetylated, and carbon terminal of the peptide is amidated.

In certain non-limiting embodiments, the peptide is $CH_3(CH_2)_{16}CONH—B—CONH_2$, wherein B is an amino acid sequence.

In certain non-limiting embodiments, B is GLWHxAWLWHyAFLASHzRLLRLLR, $1 \leq x \leq 5$, $1 \leq y \leq 5$, $1 \leq z \leq 6$, x, y, z are integers (SEQ ID NO:10).

In certain non-limiting embodiments, B is HaKbVc, $3 \leq a \leq 8$, $3 \leq b \leq 8$, $6 \leq c \leq 8$, a, b, c are integers (SEQ ID NO:11).

In certain non-limiting embodiments, B is HdRe, $8 \leq d \leq 30$, $8 \leq e \leq 20$, d, e are integers (SEQ ID NO:12).

```
In certain non-limiting embodiments,
                                    (SEQ ID NO: 4)
B is RLWRLLWRLWRWRLWRLLR.

In certain non-limiting embodiments,
                                    (SEQ ID NO: 5)
B is RLWHLLWRLWRRLHRLLR.
```

The presently disclosed and/or claimed inventive concept(s) also provides a complex comprising a cargo molecule and the peptide of any one above mentioned.

In certain non-limiting embodiments, the cargo molecule and the peptide are joined by non-covalent bonds.

In certain non-limiting embodiments, the particle size of the complex is ranged from 20 nm to 999 nm.

In certain non-limiting embodiments, the cargo molecule is a nucleic acid.

In certain non-limiting embodiments, the nucleic acid is a short interfering RNA (siRNA).

In certain non-limiting embodiments, the siRNA is complexed with the peptide at a molar ratio within the range of 1:1 to 80:1.

In certain non-limiting embodiments, the siRNA is complexed with the peptide at a molar ratio of 20:1.

In certain non-limiting embodiments, the siRNA is complexed with the peptide at a molar ratio of 40:1.

In certain non-limiting embodiments, the siRNA is complexed with the peptide at a molar ratio of 60:1.

The presently disclosed and/or claimed inventive concept(s) also provides a pharmaceutical composition comprising any one complex mentioned as above.

The presently disclosed and/or claimed inventive concept(s) also provides a kit used to deliver drugs to patient, the kit comprising a pharmaceutical composition as mentioned above, one or more electrolytes, buffers, a delivery device and a container adapted to mix one or more other agents together.

The presently disclosed and/or claimed inventive concept(s) also provides a use of the peptide mentioned as above to deliver siRNA into cells or tissues.

In certain non-limiting embodiments, the cell is ovary cell.

In certain non-limiting embodiments, the cell is a tumber cell or the tissue is tumber tissue.

The effect of the presently disclosed and/or claimed inventive concept(s) is, the peptide provided here is non-covalently coupled with siRNA to conveniently generate a peptide/siRNA complex in the form of nanoparticles. Certain peptides designed by the presently disclosed and/or claimed inventive concept(s) have both hydrophilic and hydrophobic properties, by the interaction of the hydrophilic and hydrophobic parts of the cell membrane bilayer, the delivery of siRNA into the cells and the release of siRNA in the cell was effectively enhanced, and the siRNA mediated silencing efficiency of cellular targets was improved.

The technical proposal and the advantages of the presently disclosed and/or claimed inventive concept(s) will be further described by the detailed embodiments. But in any way it is not contributed to limit the scope of the presently disclosed and/or claimed inventive concept(s).

The presently disclosed and/or claimed inventive concept(s) provides a peptide comprising a hydrophobic part and a hydrophilic part. The hydrophilic part comprises a positively charged amino acid residue. The hydrophobic part includes hydrophobic amino acid residues, stearic acid or stearic acid and hydrophobic amino acid residues. The hydrophobic amino acid residues are selected from one or more glycine (G), alanine (A), leucine (L), isoleucine (I), aromatic tryptophan (W), phenylalanine (F) and valine (V) and its derivatives. The hydrophilic part is selected from one or more arginine (R), histidine (H), lysine (k), serine (s) and its derivatives.

The peptide of the presently disclosed and/or claimed inventive concept(s) comprises peptide and peptide derivatives. Peptide derivatives comprise a peptide modified on nitrogen terminal or carbon terminal. Certain designed amphiphilic peptides possess both hydrophilic and hydrophobic moieties, therefore the peptide is bicharacteristic. Because of the peptide of the presently disclosed and/or claimed inventive concept(s) have unique sequences or groups, it is easy to generate a secondary structure by self-assembly or co-assembly.

The presently disclosed and/or claimed inventive concept(s) also provides a complex with the peptide mentioned as above and a cargo molecular. In certain non-limiting embodiments, the cargo molecule is a nucleic acid. In particular non-limiting embodiments, the nucleic acid is siRNA.

The peptide of the presently disclosed and/or claimed inventive concept(s) is to be formed into nanoparticles by co-assembly with the negatively charged siRNA. In certain non-limiting embodiments, the nanoparticles are selected from nano fibers, nano wires, nano films and nano spheres. In certain non-limiting embodiments, particle size of the complex formed by the peptide and siRNA is ranged from 20 nm to 999 nm. This is because only some certain sized nanoparticles are passable through the cell membrane. In certain non-limiting embodiments, the total number of amino acid residues contained in the peptide is ranged from 8 to 50. Peptide formed with amino acid within this range is suitable for forming nano structure after being assembled with siRNA. the peptide formed with this range of amino acid and siRNA assembled.

In one embodiment, the hydrophobic part is directly connected with the hydrophilic part. And they could also be joined via a connecting chain segment. In certain non-limiting embodiments, the connecting chain segment is one of glycine (G) and H (histidine).

In one embodiment, the peptide has a formula: GLWHxAWLWHyAFLASHzRLLRLLR, simply be regarded as GL5-M, $1 \leq x \leq 5$, $1 \leq y \leq 5$, $1 \leq z \leq 6$, x, y, z are integers (SEQ ID NO:10). In certain non-limiting embodiments, nitrogen terminal of the GL5-M is acetylated, and carbon terminal of the GL5-M is amidated.

In one embodiment, the peptide is GLWHAWLWHA-FLASHRLLRLLR (SEQ ID NO:1). In one embodiment, the peptide is CH$_3$CONH-GLWHAWLWHAFLASHR LLRLLR-CONH$_2$, simply be regarded as GL5. The GL5 is designed based on peptide GL1 that is originally reported in international patent application publication no. WO2013/075244 A1. GL1(GLWRAWLWKAFLASNWRRLLRLLR; SEQ ID NO:13) consists of a hydrophobic domain GLWRAWLWKAFLASNW (SEQ ID NO:14) and a cationic domain RRLLRLLR (SEQ ID NO:15). The amphiphilic property of this peptide makes it able to self-assemble when dissolved in water and co-assemble with negatively charged siRNA to form functionalized nanoparticles. This peptide can achieve about 95% siRNA delivery (uptake) efficiency but its gene silencing efficiency is about 50%. It is indicated that GL1 has some problems on siRNA release efficiency. Histidine (H) was reported to increase endosomal escape. Histidine was taken to replace four amino acids of GL1 to form a new peptide sequence GL5. The sequence of GL5 was further extended to a series of peptides by changing the number of H. This new series of peptides were named as GL5-M.

In certain non-limiting embodiments, a nitrogen terminal of the peptide provided by the presently disclosed and/or claimed inventive concept(s) is stearylated (simply named as STR), a carbon terminal of the peptide is amidated. STR is formed by dehydration of stearic acid and nitrogen terminal of amino. The stearic acid has been proven to have high affinity with the cell membrane, and stearylation of the peptide is able to increase the transfection efficiency of siRNA. In certain non-limiting embodiments, peptide includes histidine and its derivatives.

In certain non-limiting embodiments, peptide of the presently disclosed and/or claimed inventive concept(s) has a formula: CH$_3$(CH$_2$)$_{16}$CONH—B—CONH$_2$, B is an amino acid sequence, CH$_3$(CH$_2$)$_{16}$CONH is stearyl, and CONH$_2$ is amide. The stearyl is connected with the nitrogen terminal of the B, and the amide is connected with the carbon terminal of B.

In certain non-limiting embodiments, B has the formula: GLWHxAWLWHyAFLASHzRLLRLLR, $1 \leq x \leq 5$, $1 \leq y \leq 5$, $1 \leq z \leq 6$, x, y, z are integers (SEQ ID NO:10). The formula of the peptide is: CH$_3$(CH$_2$)$_{16}$CONH-GLWHxAWLWHyA-FLASHzRLLRLLR-CONH$_2$, named as STR-GL5-M. The introduction of stearic acid can effectively improve membrane penetration ability of the peptide.

In certain non-limiting embodiments, B has a formula: HaKbVc, $3 \leq a \leq 8$, $3 \leq b \leq 8$, $6 \leq c \leq 8$, a, b, c are integers (SEQ ID NO:11). Peptide has a formula: CH$_3$(CH$_2$)$_{16}$CONH-HaKbVc-CONH$_2$, named as STR-KV-M. In one embodiment, B is HHHKKKVVVVVV (SEQ ID NO:2), peptide is: CH$_3$(CH$_2$)$_{16}$CONH-HHHKKKVVVVVV-CONH$_2$, named as STR-KV. STR-KV peptide adopted a stearic acid as one of the hydrophobic moiety of STR-KV. Stearic acid has been proven to have high affinity with the cell membrane, and the stearylation of cell penetrating peptides has been reported to be able to increase the transfection efficiency for both plasmid DNA and siRNA. The amino acid histidine is incorporated as a linker, i.e., HHH. Histidine is a pH sensitive amino acid and can be protonated at low pH. Through the introduction of histidine moieties, peptide will act like a proton sponge that is able to disrupt endosomal membranes, resulting in the release of siRNA complexes into cytosol. The high positive charge density has been reported to result in toxicity, due to the fact that positively charged amino acid residues might interact with negatively charged cell membranes and cause aggregation and rupture on the membrane surface. Thus, three lysines are adopted in the sequences, in order to co-assemble with siRNA molecules through electrostatic interactions. Polyelectrolyte complex is formed by combining positively charged part with negative charge from phosphate group of siRNA molecule through electrostatic interactions. The complex makes the siRNA transport into the cell by stimulating non-specific cell endocytosis, and then dissociates siRNA molecules from transport carrier through "proton sponge" effect mediated endosome escape, so as to realize the transportation of siRNA. Another hydrophobic part is added to the sequence, consisting of six valine residues. The structure with two hydrophobic tails has been employed in the lipid-based gene delivery, e.g., DOPE, DOPC. Lipid tails are thought to be important for effective gene delivery, and can assist in cellular uptake through interacting with the hydrophobic tails in the lipid bilayer of the cells. The lipids consisting of two hydrophobic tails have been reported to have lower critical aggregation concentrations than single-chain lipids. The hydrophobic block with six valine residues is adopted to mimic the structure of two lipid tails. It is beneficial to penetrate the cell membrane.

In certain non-limiting embodiments, B has a formula: HdRe, $8 \leq d \leq 30$, $8 \leq e \leq 20$, d, e are integers (SEQ ID NO:12). Peptide has a formula: CH$_3$(CH$_2$)$_{16}$CONH—HdRe—CONH$_2$, named as STR-HR-M. In one embodiment, B is HHHHHHHHHHHHHHHHHHHHRRRRRRRRR (SEQ ID NO:3), peptide is CH$_3$(CH$_2$)$_{16}$CONH- HHHHHHHHHHHHHHHHHRRRRRRRR-CONH$_2$, named as STR-HR. The STR-HR peptide is a novel molecular sequence designed by high throughput screening. STR-HR consists of three parts: hydrophobic stearic acid, a hydrophobic tail, a segment of sixteen histidines (H16); and eight arginines (R8), a hydrophilic segment. The sequence R8 is a cell penetrating peptide, which can strongly interact with cell membranes. Stearylation and the use of oligohistidines may facilitate the endosomal escape of peptide/siRNA complexes.

In one embodiment, B is RLWRLLWRLWRRLWRLLR (SEQ ID NO:4), the peptide is CH$_3$(CH$_2$)$_{16}$CONH-RLWRLLWRLWRRLWRLLR-CONH$_2$, named as STR-C6M1.

In one embodiment, B is RLWHLLWRLWRRLHRLLR (SEQ ID NO:5), the peptide is CH$_3$(CH$_2$)$_{16}$CONH-RLWHLLWRLWRRLHRLLR-CONH$_2$, named as STR-C6M1.

STR-C6M1 and STR-C6M3 are derivatives from the peptides C6M1 and C6M3, respectively. C6M1 is RLWRLLWRLWRRLWRLLR (SEQ ID NO:4), C6M3 is RLWHLLWRLWRRLHRLLR (SEQ ID NO:5). C6M1 and C6M3 were originally reported in international patent application publication no. WO2013/075244 A1. Arginine rich peptides are reported to be capable of delivering siRNAs into cells with high efficiency and low toxicity, while at least five arginine residues are required to maintain the transfection efficiency. Hydrophobic residues such as leucine are also included in C6 sequence. These hydrophobic amino acids can facilitate the translocation of peptide by interacting with the hydrophobic tails in the lipid bilayer or assisting in pore formation in the cell membrane. It has been found that alanine, leucine and histidine are found abundantly in the helical regions of proteins. They indicate that leucine is the strongest structure forming residue in the proteins investigated. To increase its solubility and transfection efficiency, we substituted some amino acid residues with aromatic tryptophan and histidine. Stearic acid is one of the fatty acids occurring abundantly in the body and has high interaction ability with the cell membrane. Modified C6M3 and C6M1 and stearic acid further enhance penetration to the cell membrane.

The presently disclosed and/or claimed inventive concept(s) also provides a pharmaceutical composition. The pharmaceutical composition comprises the complexes of peptide and cargo molecule. In certain non-limiting embodiments, the cargo molecule is selected from one or more siRNA, miRNA and shRNA. In particular non-limiting embodiments, the cargo molecule is siRNA. In one embodiment, the pharmaceutical composition of the presently disclosed and/or claimed inventive concept(s) can reduce the level of endogenous protein in cell or tissue. In certain non-limiting embodiments, the cell is a tumber cell or the tissue is tumber tissue.

The presently disclosed and/or claimed inventive concept(s) also provides a kit used to deliver drugs for patient, the kit comprises a pharmaceutical composition, one or more electrolytes, buffers, a delivery device and a container that mixes one or more other agents together. The kit also includes instructions for using of the pharmaceutical, a mixture of pharmaceutical and other reagents, and the description to be given to the user.

The presently disclosed and/or claimed inventive concept(s) also provides a use of the peptide as a carrier to deliver siRNA to cells or tissues. In one embodiment, the cell is CHO. In one embodiment, the cell is a tumber cell. In one embodiment, the tissue is tumber tissue.

Experimental Apparatus and Sample Preparation

1. Experimental Apparatus

The molar concentration of siRNA was measured by the nucleic acid protein analyzer Nanodrop ND-1000, purchased from the ThermoFisher company. The number of mRNA was measured by Mx3005P Real-Time PCR System Agilent Co (Wilmington, USA).

2. Sample

Glyceraldehyde-3-phosphate dehydrogenase (GAPDH) are used as the target gene. Glyceraldehyde-3-phosphate dehydrogenase (GAPDH) is a housekeeping gene widely expressed in diverse tissues and cell types and functions in a variety of cellular processes. The corresponding siRNA, i.e., Silencer® GAPDH siRNA (Human, Mouse, Rat), was purchased from Ambion. All peptide compounds was purchased from Pepscan Systems (Leystad, Netherlands).

3. Cell Test

An adult CHO tissue CHO-K1 (ATCC CCL-61) has been used as a cell test object.

4. Detection of mRNA

Real-time RT-PCR is at present the most sensitive method for the detection of low abundance mRNA. Total RNA from the cells was extracted with TRIzol reagent, then treated with chloroform and 2-propanol as recommended by the manufacturer. The RNA concentrations were measured by Nanodrop. All the RNAs were reverse transcribed with Bio-Rad iScript cDNA synthesis kit according to the protocol. The cDNA synthesis was primed with a unique blend of oligo (dT) and random primers. The sequences of the primers used for the mouse GAPDH gene are 5'-TTGCTGTTGAAGTCGCAGGAG-3' (SEQ ID NO:6) and 5'-TGTGTCCGTCGTGGATCTGA-3' (SEQ ID NO:7) (Sigma, Oakville, Ontario, Canada). Cyclophilin, a housekeeping gene, was used as an internal control to normalize the GAPDH gene expression. Mouse cyclophilin mRNA amplified using the following primers: 5'-AGGGTTTCTC-CACTTCGATCTTGC-3' (SEQ ID NO:8) and 5'-AG-ATGGCACAGGAGGAAAGAGCAT-3' (SEQ ID NO:9) (Sigma, Oakville, Ontario, Calif.).

5. Cytotoxicity Test

CHO-K1 cells were seeded at 5,000-8,000 cells/well in clear, flat-bottomed, 96-well plates in triplicate and grown for 24 h at 37° C. with 5% $CO_2$. The complexes or control samples were added to the cells in 150 µl of standard media and the cells were incubated for 48 h. The CCK8 assay was used to determine cell viability, according to the manufacturer's instructions. Briefly, 110 µl of CCK8 stock was added to each well and incubated for 2 h at 37° C. in 5% $CO_2$. Then, the cultures were removed from the incubator and the absorbance at 570 nm was read on a plate reader (FLUOstar OPTIMA, BMG, Germany). The background absorbance of the multiwell plates at 690 nm was determined and subtracted from the 570 nm measurement. The results obtained from triplicate wells were averaged and normalized using the value obtained for non-treated cells.

All the professional and scientific terms used in the presently disclosed and/or claimed inventive concept(s) are the same as that of the person skilled in the field. In addition, any method or material which is similar or equivalent to the written contents can be applied to the method of the presently disclosed and/or claimed inventive concept(s). The particular (but non-limiting) embodiments illustrated here are only for examples.

Combining with the following example, a more detailed description of the content of the presently disclosed and/or claimed inventive concept(s) is provided. It should be understood that the implementation of the presently disclosed and/or claimed inventive concept(s) is not limited to the detailed embodiments as below, and any amendments and/or changes under the spirit of the presently disclosed and/or claimed inventive concept(s) shall fall into the protection scope of the presently disclosed and/or claimed inventive concept(s). In this presently disclosed and/or claimed inventive concept(s), unless specified, all percentages in the description are directed to weight ration, all equipments and materials can be purchased from the market or commonly used in the industry.

Example 1-1

GL5 peptide is used as the carrier of siRNA delivery in this embodiment.
Preparation of siRNA/GL5 GAPDH Complex
GL5 peptide with concentration of 1000 nM and GAPDH siRNA with concentration of 50 nM were dissolved respectively in a serum free Opti-MEM solution with the molar ratio of 20:1. Then the gene was added into the peptide solution by the method of uniform mixing. After standing half an hour, the carrier is ready in a fully stable status to be measured and for further use.
In Vivo Transfection of siRNA/GL5 GAPDH Complex
The cells were seeded with a confluency of 35,000-40,000 cells/well in F12K medium with 10% FBS without antibacterial agents, 24 hrs before transfection. On the next day, rinse the cells with PBS buffer before transfection and add 200 µl of Opti-MEM. 100 µl of the complex solution (GAPDH siRNA-peptide) were added to each well. The cells were incubated with the complex at 37° C. in an incubator. After 4 hours, 300 µl F12-K with 20% FBS was added without removing the transfection mixture. The cells were rinsed and lysed 48 hours after the start of transfection.
Detect mRNA content in cells by Real-time RT-PCR, and proceed the cytotoxicity test.

Example 1-2

GL5 peptide with concentration of 2000 nM and GAPDH siRNA with concentration of 50 nM are used to prepare of GL5/siRNA complex with the molar ratio of 40:1, the preparation method is same as that of example 1-1.
In vivo transfection of GL5/siRNA complex, the method is same as that of example 1-1.
Detect mRNA content in cells by Real-time RT-PCR, and proceed the cytotoxicity test.

Example 2-1

STR-KV peptide is used as the carrier of siRNA delivery in this embodiment.
STR-KV peptide with concentration of 1500 nM and GAPDH siRNA with concentration of 50 nM are used to prepare of STR-KV/siRNA complex with the molar ratio of 30:1, the preparation method is same as that of example 1-1.
In vivo transfection of STR-KV/siRNA complex, the method is same as that of example 1-1.
Detect mRNA content in cells by Real-time RT-PCR, and proceed the cytotoxicity test.

Example 2-2

STR-KV peptide is used as the carrier of siRNA delivery in this embodiment.
STR-KV peptide with concentration of 2250 nM and GAPDH siRNA with concentration of 50 nM are used to prepare of STR-KV/siRNA complex with the molar ratio of 45:1, the preparation method is same as that of example 1-1.
In vivo transfection of STR-KV/siRNA complex, the method is same as that of example 1-1.
Detect mRNA content in cells by Real-time RT-PCR, and proceed the cytotoxicity test.

Example 2-3

STR-KV peptide is used as the carrier of siRNA delivery in this embodiment.
STR-KV peptide with concentration of 3000 nM and GAPDH siRNA with concentration of 50 nM are used to prepare of STR-KV/siRNA complex with the molar ratio of 60:1, the preparation method is same as that of example 1-1.
In vivo transfection of STR-KV/siRNA complex, the method is same as that of example 1-1.
Detect mRNA content in cells by Real-time RT-PCR, and proceed the cytotoxicity test.

Example 3-1

STR-HR peptide is used as the carrier of siRNA delivery in this embodiment.
STR-HR peptide with concentration of 3000 nM and GAPDH siRNA with concentration of 100 nM are used to prepare of STR-KV/siRNA complex with the molar ratio of 30:1, the preparation method is same as that of example 1-1.
In vivo transfection of STR-HR/siRNA complex, the method is same as that of example 1-1.
Detect mRNA content in cells by Real-time RT-PCR, and proceed the cytotoxicity test.

Example 3-2

STR-HR peptide is used as the carrier of siRNA delivery in this embodiment.
STR-HR peptide with concentration of 4500 nM and GAPDH siRNA with concentration of 100 nM are used to prepare of STR-KV/siRNA complex with the molar ratio of 45:1, the preparation method is same as that of example 1-1.
In vivo transfection of STR-HR/siRNA complex, the method is same as that of example 1-1.
Detect mRNA content in cells by Real-time RT-PCR, and proceed the cytotoxicity test.

Example 3-3

STR-HR peptide is used as the carrier of siRNA delivery in this embodiment.
STR-HR peptide with concentration of 6000 nM and GAPDH siRNA with concentration of 100 nM are used to prepare of STR-KV/siRNA complex with the molar ratio of 60:1, the preparation method is same as that of example 1-1.
In vivo transfection of STR-HR/siRNA complex, the method is same as that of example 1-1.
Detect mRNA content in cells by Real-time RT-PCR, and proceed the cytotoxicity test.

Example 4-1

STR-C6M1 peptide is used as the carrier of siRNA delivery in this embodiment.
STR-C6M1 peptide with concentration of 2000 nM and GAPDH siRNA with concentration of 50 nM are used to prepare of STR-KV/siRNA complex with the molar ratio of 40:1, the preparation method is same as that of example 1-1.

In vivo transfection of STR-C6M1/siRNA complex, the method is same as that of example 1-1.

Detect mRNA content in cells by Real-time RT-PCR, and proceed the cytotoxicity test.

Example 4-2

STR-C6M1 peptide is used as the carrier of siRNA delivery in this embodiment.

STR-C6M1 peptide with concentration of 3000 nM and GAPDH siRNA with concentration of 50 nM are used to prepare of STR-KV/siRNA complex with the molar ratio of 60:1, the preparation method is same as that of example 1-1.

In vivo transfection of STR-C6M1/siRNA complex, the method is same as that of example 1-1.

Detect mRNA content in cells by Real-time RT-PCR, and proceed the cytotoxicity test.

Example 5-1

STR-C6M3 peptide is used as the carrier of siRNA delivery in this embodiment.

STR-C6M3 peptide with concentration of 2000 nM and GAPDH siRNA with concentration of 50 nM are used to prepare of STR-KV/siRNA complex with the molar ratio of 40:1, the preparation method is same as that of example 1-1.

In vivo transfection of STR-C6M3/siRNA complex, the method is same as that of example 1-1.

Detect mRNA content in cells by Real-time RT-PCR, and proceed the cytotoxicity test.

Example 5-2

STR-C6M3 peptide is used as the carrier of siRNA delivery in this embodiment.

STR-C6M3 peptide with concentration of 3000 nM and GAPDH siRNA with concentration of 50 nM are used to prepare of STR-KV/siRNA complex with the molar ratio of 60:1, the preparation method is same as that of example 1-1.

In vivo transfection of STR-C6M3/siRNA complex, the method is same as that of example 1-1.

Detect mRNA content in cells by Real-time RT-PCR, and proceed the cytotoxicity test Contrast Example 1

Lipid (lipofactamine 2000, lipo) is used as the carrier of siRNA delivery in this embodiment.

Prepare lipid/siRNA complex, the preparation method is same as that of example 1-1.

In vivo transfection of Lipid/siRNA GAPDH complex, the method is same as that of example 1-1.

Figure 2:
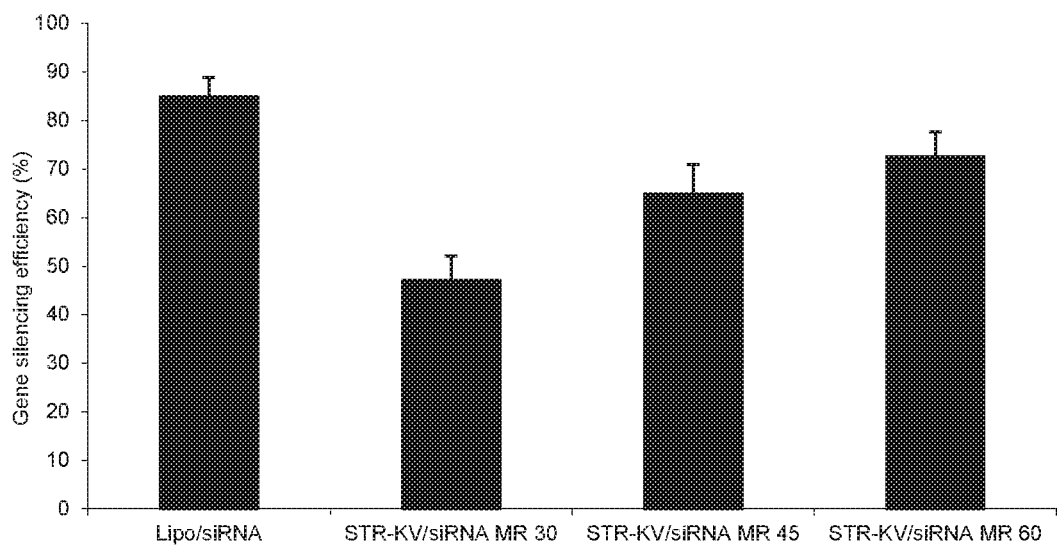
FIG. 2 illustrates the silencing efficiency of STR-KV/siRNA complexes with molar ratio 30/1, 40/1, and 60/1 in CHO cells with siRNA concentrations of 50 nM.
Figure 3:
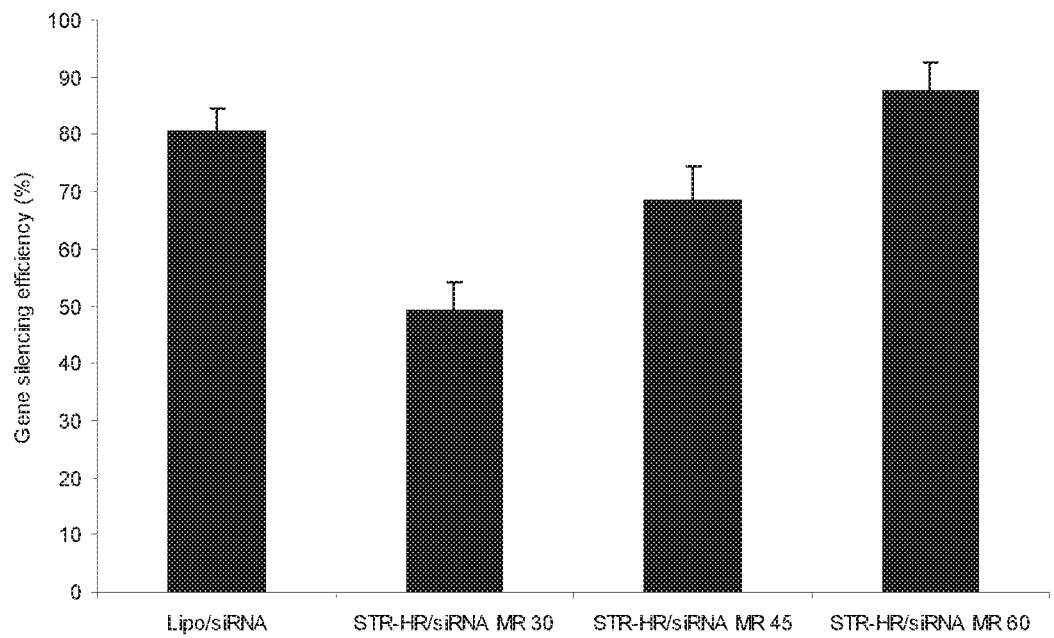
FIG. 3 illustrates the silencing efficiency of STR-HR/siRNA complexes with molar ratio 30/1, 45/1, and 60/1 in CHO cells with siRNA concentrations of 100 nM.
Figure 4:
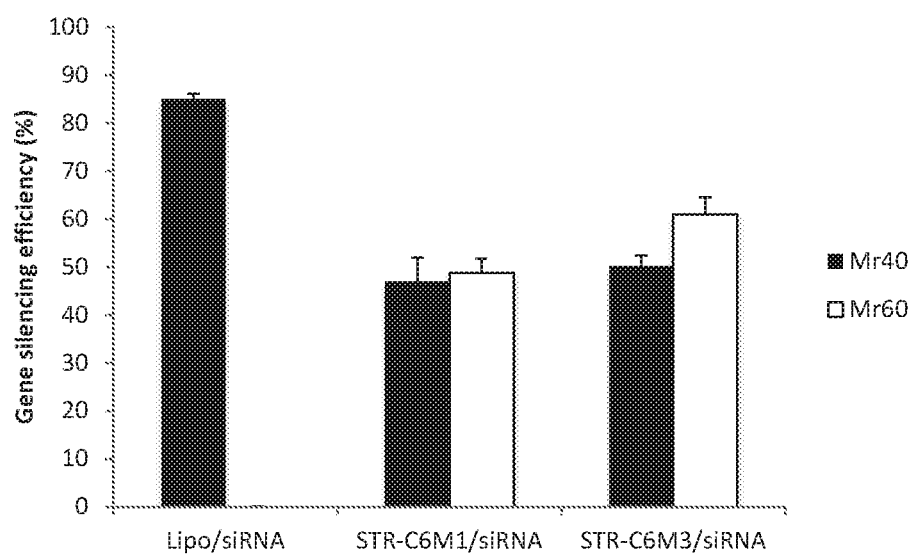
FIG. 4 illustrates the silencing efficiency of STR-C6M1/siRNA and STR-C6M3/siRNA complexes with molar ratio 40/1, and 60/1 in CHO cells with siRNA concentrations of 50 nM.

Detect mRNA content in cells by Real-time RT-PCR, and proceed the cytotoxicity test RT-PCR results of GAPDH siRNA complexed with different peptides at different molar ratio are shown in FIGS. 1 to 4. FIG. 1 shows the intracellular silencing of GAPDH gene in CHO cells where siRNA were complexed with GL5 at a molar ratio of 20/1 and 40/1. FIG. 2 shows the intracellular silencing of GAPDH gene in CHO cells where siRNA were complexed with STR-KV at a molar ratio of 30/1, 40/1 and 60/1. FIG. 3 shows the silencing efficiency of STR-HR/siRNA complexes with molar ratio 30/1, 45/1, and 60/1 in CHO cells. FIG. 4 shows the silencing efficiency of STR-C6M1/siRNA and STR-C6M3/siRNA complexes with molar ratio 40/1, and 60/1 in CHO cells. The results shown in FIGS. 1 to 4 correspond to an average of at least three separate experiments.

Figure 5:
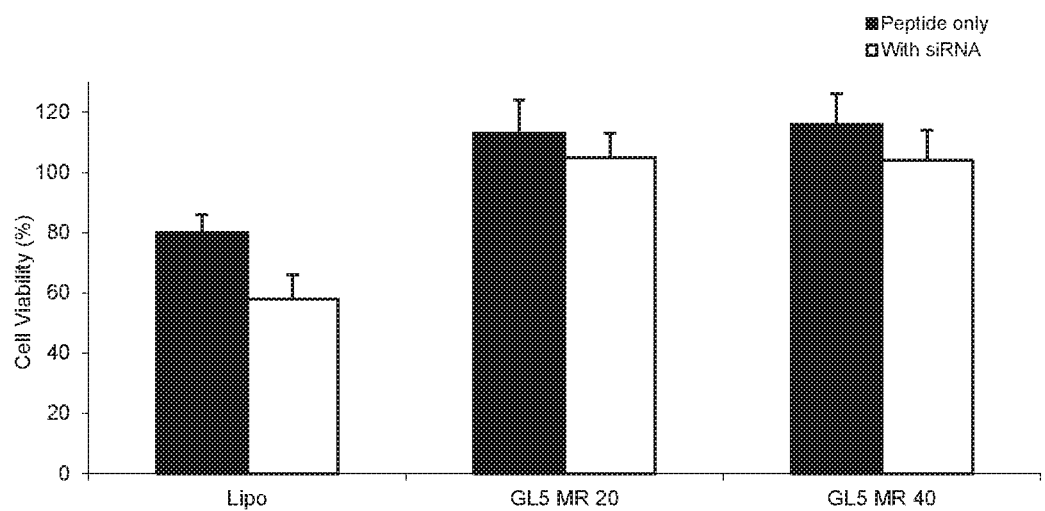
FIG. 5 illustrates cytotoxicity of GL5/siRNA complexes with molar ratio 20/1 and 40/1 in CHO cells with siRNA concentrations of 50 nM.
Figure 6:
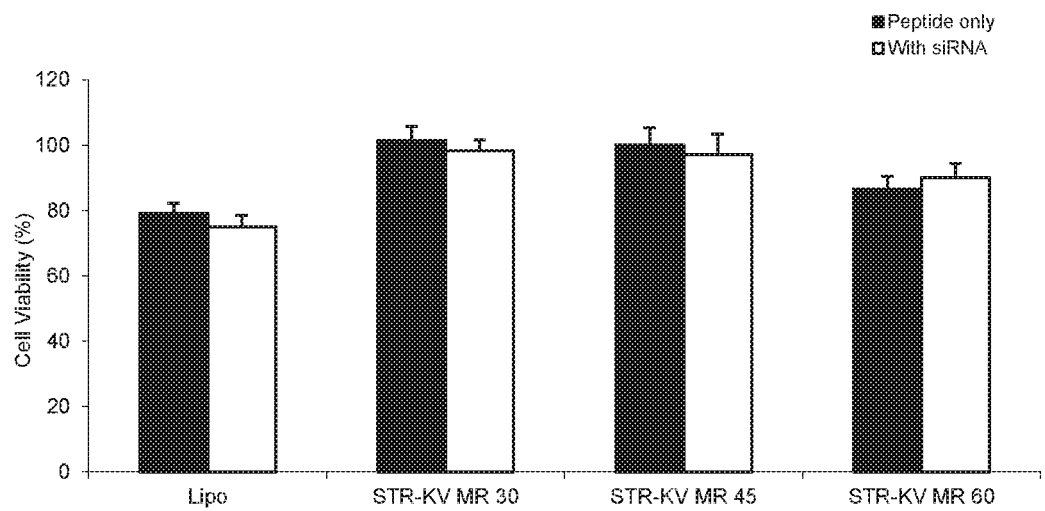
FIG. 6 illustrates cytotoxicity of STR-KV/siRNA complexes with molar ratio 30/1, 45/1, and 60/1 in CHO cells with siRNA concentrations of 50 nM.
Figure 7:
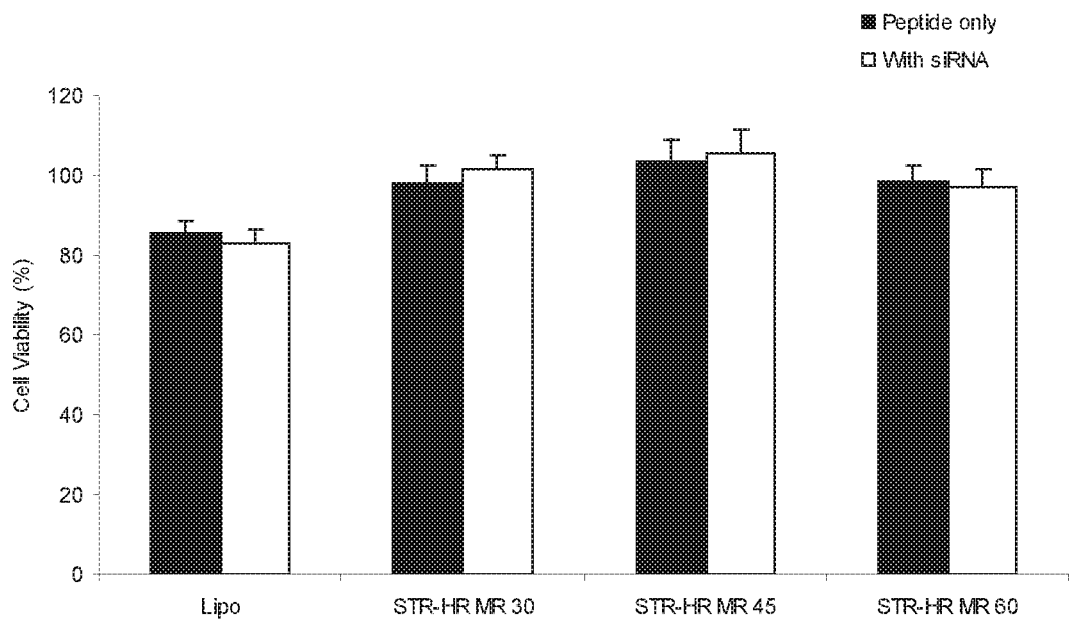
FIG. 7 illustrates cytotoxicity of STR-HR/siRNA complexes with molar ratio 30/1, 45/1, and 60/1 in CHO cells with siRNA concentrations of 100 nM.
Figure 8:
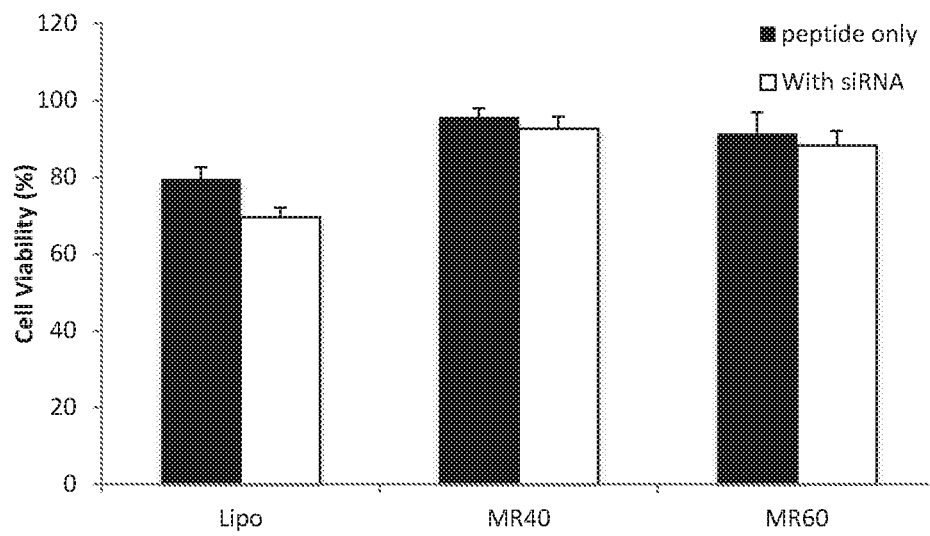
FIG. 8 illustrates cytotoxicity of STR-C6M1/siRNA and STR-C6M3/siRNA complexes with molar ratio 40/1 and 60/1 in CHO cells, with siRNA concentrations of 50 nM.

Cytotoxicity results of GAPDH siRNA complexed with different peptides at molar ratio 20 to 60 are shown in FIGS. 5 to 8. FIG. 5 shows the cytotoxicity in CHO cells where siRNA were complexed with GL5 at a molar ratio of 20/1 and 40/1. FIG. 6 shows the intracellular silencing of GAPDH gene in CHO cells where siRNA were complexed with STR-KV at a molar ratio of 30:1, 45:1 and 60:1. FIG. 7 shows the silencing efficiency of STR-HR/siRNA complexes with molar ratio 30/1, 45/1, and 60/1 in CHO cells. FIG. 8 shows the cytotoxicity in CHO cells where siRNA were complexed with STR-C6M1 and STR-C6M3 at a molar ratio of 40/1 and 60/1. The results shown in FIGS. 5 to 8 correspond to an average of at least three separate experiments.

With reference to FIG. 1 and FIG. 5, when the molar ratio of GL5 and siRNA is 20/1 and 40/1, the gene silencing efficiency of siRNA is 41% and 65%, respectively, which is lower than that of the lipid transfected siRNA. But for both GL5 itself and the GL5/siRNA complex, the cell survival rates are about 105% and 104% respectively, which are much higher than that of the lipid or lipid/siRNA complex, which is 58%. GL5 peptide of the presently disclosed and/or claimed inventive concept(s) is modified based on GL1 peptide in the prior art. Four positively charged histidine are taken to replace four amino acids on the basis of GL1 to get GL5 peptide. And histidine has been proven to have high endosomal escape ability, it delivers the siRNA entered into the cell to release from endosomal and into cytoplasm, thereby results silencing effect with mRNA. According to disclosure of international patent application Publication No. WO2013/075244A1, gene silencing efficiency of siRNA with GL1 carrier is about 50%. Therefore, comparing with the prior art, silencing efficiency and biological compatibility of the presently disclosed and/or claimed inventive concept(s) have got great enhancement.

Shown as FIG. 2 and FIG. 6, the gene silencing efficiencies are increased with molar ratio of STR-KV/siRNA increase from 30/1 to 45/1 and 60/1, which are 47%, 65%, 73%, respectively. They are close to the gene silencing efficiency of lipid/siRNA complex under the same condition, which is 85%. Similarly, the cell survival rates of STR-KV and STR-KV/siRNA are approximately 98%, 97% and 90%, respectively, which was slightly decreased with the increase of molar ratio, but were higher than that of the lipid or lipid/siRNA complex, which is 75%. In summary, the peptide STR-KV designed by the presently disclosed and/or claimed inventive concept(s) has good siRNA delivery performance and excellent biocompatibility, and it is suitable for application in vivo.

Shown as FIG. 3 and FIG. 7, the gene silencing efficiencies of STR-HR/siRNA are increased with the molar ratio increase from 30/1, to 45/1 and 60/1, which are 50%, 67%, 87% respectively. They are higher than that of the lipid transfected siRNA at the molar ratio of 60/1, which is 85%. The cell survival rate of STR-HR and STR-HR/siRNA complex reaches the maximum when the molar ratio is 45/1, but the cell survival rates in the three molar ratio are higher than that of the lipid or lipid/siRNA complex. At the same time, it was found that the absorption efficiency of STR-HR was higher than that of lipid 2000 according to result of cell absorption test. Silencing efficiency of STR-HR/siRNA complex is similar to that of lipid 2000/siRNA complex. Cytotoxicity of STR-HR per molar ratio for silencing efficiency test was not higher than that of lipid 2000. In addition, by dynamic light scattering experiments, it is proven that particles size of STR-HR and siRNA complexes are all in a range from 50 nm to 150 nm when molar ratio range of STR-HR/siRNA is within 15-60. Such particle size range is suitable for applications in vivo through intravenous control.

Molar ratio range of STR-HR/siRNA is from 15 to 60, Zeta potential is from 21 mv to 28 my companying with the molar ratio increase. As described above, the peptide STR-HR designed by the presently disclosed and/or claimed inventive concept(s) has excellent siRNA transfer performance and biocompatibility, wherein, STR-HR/siRNA with a molar ratio of 60/1 has the best effect.

Shown as FIG. 4 and FIG. 8, the gene silencing efficiencies of STR-C6M1/siRNA are increased with the molar ratio increase from 40/1, to 60/1, which are 47% and 49% respectively. They are higher than that of the lipid transfected siRNA. The cell survival rates of STR-C6M1 and STR-C6M1/siRNA are approximately 93% and 88% respectively, which was slightly decreased with the increase of molar ratio, but were much higher than that of lipid or lipid/siRNA complex. In addition, in international patent application WO2013075244, cell survival rate of C6M3/siRNA transfected with molar ratio of 40/1 is less than 40%, which was far less than that of the presently disclosed and/or claimed inventive concept(s). Also, shown as FIG. 4 and FIG. 8, the gene silencing efficiencies of STR-C6M3/siRNA are increased with the molar ratio increase from 40/1 to 60/1, which are 50%, 61% respectively. They are lower than that of the lipid transfected siRNA. The cell survival rates of STR-C6M3 and STR-C6M3/siRNA are slightly decreased with the molar ratio increase, which are approximately 96% and 91%, respectively. But they are higher than that of the lipid or lipid/siRNA complex. In addition, in international patent application WO2013075244, cell survival rate of C6M3/siRNA transfected with molar ratio of 40/1 is less than 50%, which was far less than the cell survival rate of the presently disclosed and/or claimed inventive concept(s). It is illustrated that after N terminal of the peptide is stearic acylated, the peptide STR-C6M1 and STR-C6M3 have good siRNA delivery performance and excellent biocompatibility, and are suitable for application in vivo.

In conclusion, the presently disclosed and/or claimed inventive concept(s) provides a peptide. It can be coupled non-covalently with siRNA by self-assemble or co-assemble, and to be formed into nanostructures and to transfer siRNA into the cytoplasm. Because of quickly protonated, biodegradable and bicharacteristic peptide or peptide carrier can effectively combine and protect siRNA molecules to enhance cellular uptake of siRNA molecules, and improve its stability and targeting, and effectively release siRNA molecules, and reach the purpose of treatment. Experiment result shows that, silence efficiency of SiRNA is obviously improved, the peptide has the low toxicity and good biocompatibility. The peptide carrier of the presently disclosed and/or claimed inventive concept(s) has better advantage and application prospect in siRNA drug delivery.

The above mentioned are only particular, non-limiting embodiments of the presently disclosed and/or claimed inventive concept(s), they are not intended to be limited to the presently disclosed and/or claimed inventive concept(s), any modifications, equivalent replacements and improvements within the spirit and principle of the presently disclosed and/or claimed inventive concept(s) shall be included in the protection scope of the presently disclosed and/or claimed inventive concept(s).

What is claimed is:

1. A peptide having the sequence $CH_3(CH_2)_{16}CONH-B-CONH_2$, wherein B is SEQ ID NO:4 or 5.

2. A complex comprising:
a cargo molecule; and
a peptide having the sequence $CH_3(CH_2)_{16}CONH-B-CONH_2$, wherein B is SEQ ID NO:4 or 5.

3. The complex according to claim 2, wherein the cargo molecule and the peptide are coupled non-covalently.

4. The complex according to claim 2, wherein the particle size of the complex is in a range of from 20 nm to 999 nm.

5. The complex according to claim 2, wherein the cargo molecule is a nucleic acid.

6. The complex according to claim 5, wherein the nucleic acid is a short interfering RNA (siRNA).

7. The complex according to claim 6, wherein the siRNA is complexed with the peptide at a molar ratio within a range of from 1:1 to 80:1.

8. The complex according to claim 6, wherein the siRNA is complexed with the peptide at a molar ratio of 20:1.

9. The complex according to claim 6, wherein the siRNA is complexed with the peptide at a molar ratio of 40:1.

10. The complex according to claim 6, wherein the siRNA is complexed with the peptide at a molar ratio of 60:1.

11. A pharmaceutical composition containing a complex comprising:
a cargo molecule; and
a peptide having the sequence $CH_3(CH_2)_{16}CONH-B-CONH_2$, wherein B is SEQ ID NO:4 or 5.

12. A kit used to deliver drugs to a patient, wherein the kit comprises:
a pharmaceutical composition comprising a complex comprising:
a cargo molecule; and
a peptide having the sequence $CH_3(CH_2)_{16}CONH-B-CONH_2$, wherein B is SEQ ID NO:4 or 5;
one or more electrolytes;
one or more buffers;
a delivery device; and
a container adapted to mix one or more other agents together.

13. The kit according to claim 12, wherein the cargo molecule and the peptide are coupled non-covalently.

14. The kit according to claim 12, wherein the particle size of the complex is in a range of from 20 nm to 999 nm.

15. The kit according to claim 12, wherein the cargo molecule is a nucleic acid.

16. The kit according to claim 15, wherein the nucleic acid is a short interfering RNA (siRNA).

17. The kit according to claim 16, wherein the siRNA is complexed with the peptide at a molar ratio within a range of from 1:1 to 80:1.

18. The kit according to claim 16, wherein the siRNA is complexed with the peptide at a molar ratio in a range of from 20:1 to 60:1.

19. The kit according to claim 16, wherein the siRNA is complexed with the peptide at a molar ratio of 20:1 or 40:1.

20. A method, comprising:
delivering the pharmaceutical composition of claim 11 to a patient.

* * * * *

UNITED STATES PATENT AND TRADEMARK OFFICE
CERTIFICATE OF CORRECTION

| | |
|---|---|
| PATENT NO. | : 11,306,313 B2 |
| APPLICATION NO. | : 16/751783 |
| DATED | : April 19, 2022 |
| INVENTOR(S) | : Pu Chen et al. |

It is certified that error appears in the above-identified patent and that said Letters Patent is hereby corrected as shown below:

In the Specification
Column 13, Line 8: Delete "28 my" and replace with -- 28 mv --

Signed and Sealed this
Thirty-first Day of May, 2022

*Katherine Kelly Vidal*

Katherine Kelly Vidal
*Director of the United States Patent and Trademark Office*